United States Patent [19]

Miyashita et al.

[11] Patent Number: 5,120,743
[45] Date of Patent: Jun. 9, 1992

[54] CYCLIC ANTHRANILIC ACID ACETIC ACID DERIVATIVES AND PROCESS FOR THE PREPARATION

[75] Inventors: Mitsutomo Miyashita, Okaya; Yasushi Kohno, Oyama; Eisuke Kojima, Koga; Koji Saito, Oyama, all of Japan

[73] Assignee: Kyorin Pharmaceutical Co., Ltd., Tokyo, Japan

[21] Appl. No.: 536,756

[22] Filed: Jun. 12, 1990

[30] Foreign Application Priority Data

Jun. 13, 1989 [JP] Japan .................. 1-149989

[51] Int. Cl.$^5$ .................. A61K 31/47; C07D 215/00
[52] U.S. Cl. .................. 514/311; 546/174
[58] Field of Search .................. 546/174, 173, 168; 514/311

[56] References Cited

U.S. PATENT DOCUMENTS

| | | | |
|---|---|---|---|
| 4,234,733 | 11/1980 | Isshiki et al. | 546/174 |
| 4,956,372 | 9/1990 | Kojima et al. | 514/311 |
| 4,960,892 | 10/1990 | Kreft, III et al. | 546/174 |

FOREIGN PATENT DOCUMENTS 203352 8/1989 Japan .................. 540/174

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

Cyclic anthranilic acid acetic acid derivatives of the following formula,

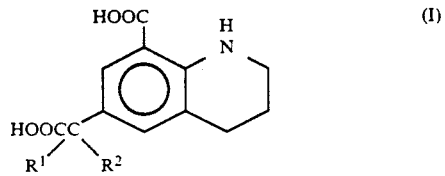

wherein $R^1$ and $R^2$ each independently indicate a hydrogen atom, lower alkyl group having 1 to 3 carbon atoms; their acid or alkali salts thereof are useful as drugs treat autoimmune diseases, antirheumatic agents and therapeutic or prophylactic agents to treat metabolic bone diseases.

8 Claims, No Drawings

CYCLIC ANTHRANILIC ACID ACETIC ACID DERIVATIVES AND PROCESS FOR THE PREPARATION

DETAILED DESCRIPTION OF THE INVENTION

This invention is concerned with certain novel cyclic anthranilic acid acetic acid derivatives, their acid and alkali salts thereof and the process for their preparation thereof. This invention is also concerned with the use of these novel compounds as antirheumatic agents, drugs for treating autoimmune diseases, and drugs which have both therapeutic and prophylactic effects on metabolic bone diseases.

Chronic diseases related to immune responses include rheumatoid arthritis and other autoimmune diseases (systemic lupus erythematosus, psoriatic arthritis, atopic dermatitis, ankylosing spondylitis). These diseases are considered to be caused by bacteria, virus or autoantigens or by an aberration in cytokine regulation of T cells. Especially, patients with rheumatoid arthritis demonstrate various immune abnormalities including reduced functions of suppressor T cells and hyperactivity of B cells.

Non-steroidal antiinflammatory drugs are widely used as first choice drugs in the therapy of rheumatoid arthritis and other diseases due to immunological disorders. While these drugs offer symptomatic relief for patients with these diseases, they fail to alter the underlying immunological dysfunction or the overall course of the disease process. Furthermore, serious side effects from prolonged use of these drugs have also been well documented.

On the other hand, second choice antirheumatic drugs, such as gold salt and D-penicillamine have little acute antiinflammatory effects, but they appear to show or halt the tissue destruction and more especially the progression of articular damage. They also have immunomodulatory effects. However, it is necessary to improve the safety and other aspects of these drugs, because of the higher incidence of side effects that have been observed in 40–50% of the patients treated with these drugs.

Metabolic bone diseases as generic term include osteoporosis, osteomalacia and ostetic fibrous. In patients with these diseases, there are morbid changes in weight, constitution and structure of bone as a result of the failure of the systemic bone formation and resorption process. This is caused by abnormalities in the somatological regulatory system due to various hormones or vitamins and by congenital or acquired abnormalities of the functions of the osteocytes. It is also associated with abnormal calcium and phosphorus metabolism. Vitamin D, calcium, calcitonin and phosphorus are used as therapeutic drugs, but their effectiveness has not been clearly proven and development of a superior drug has been strongly desired.

As a result of our research into the development of an antirheumatic agent, we have found that novel cyclic anthranilic acid acetic acid derivatives represented by a general formula (I) and their acid and alkali salts thereof, have potent therapeutic effects upon rheumatic arthritis without inhibiting cyclooxygenase activity. We have proved the superiority in the safety as well as in the effectiveness of these compounds. We have also found that these compounds of this invention have inhibitory effects on bone damage.

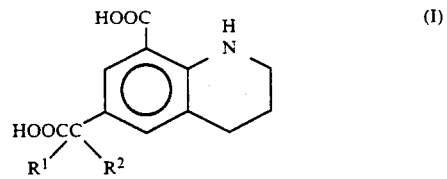

wherein $R^1$ and $R^2$ each independently indicate a hydrogen atom, lower alkyl group having 1 to 3 carbon atoms.

The compounds which structurally resemble the compounds represented by a general formula (I) have been published in Japan Kokai Sho 58-116466 (Nippon Zoki Pharmaceutical Co., Ltd.), and in U.S. Pat. No. 3,778,511 (Ciba-Geigy Corporation). The compounds in these literatures have been described to have antiinflammatory action, but the potency of such compounds are not satisfactory. Moreover, any claim of these patents never include the compounds of this invention.

We have published the compounds represented by a following general formula in EP-A-0 310 096,

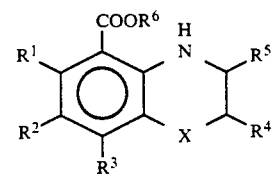

wherein $R^1$, $R^2$ and $R^3$ each independently indicate a hydrogen atom, a halogen atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoylmethyl group which may be substituted, methylthio group, phenylethynyl group which may be substituted, ethynyl group which may be substitute, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzyl group; $R^6$ indicates a hydrogen atom, lower alkyl group having 1 to 3 carbon atoms or benzyl group; X indicates a methylene group, oxygen atom, sulfur atom, sulfinyl group or sulfonyl group. The compounds of this invention, however, have not been included in above patent and have unexpectedly higher potency.

Next, we will describe the process for their preparation of the compounds of this invention.

Cyclic anthranilic acids that amino groups looped benzene rings have been synthesized by oxidizing 1,7-trimethyleneisatins with hydrogen peroxide in aqueous alkali medium (E. Ziegler et al., Monatsh. Chem., 94, 698 (1963), ibid 95, 59 (1964)), or by reducing quinoline-8-carboxylic acid (C. Satyendranath et al, J. Annamalai Univ., 2, 227 (1933)).

But, all of the literatures have included the very limited compounds and no mentions have been made on pharmacological activity.

According to the invention, the compounds represented by the general formula (I) are prepared from the compounds represented by the general formula (II) by hydrolysing and then by decarbonylation. Moreover, they can be prepared by the compounds represented by the general formula (II) to hydrolyse with a little excess mole of suitable alkali solution such as, for example, sodium hydroxide or potassium hydroxide, in a suitable solvent such as, for example, water or aqueous alcohol and followed by oxidization with more than equal mole of a mild oxidant such as, for example, hydrogen peroxide solution or acetic peracid. Preferably, reaction temperature is 0° to 50° C. and reaction time is 0.5 to 3 hours.

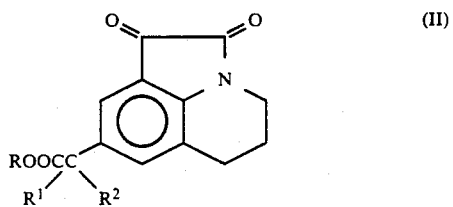

wherein R, $R^1$ and $R^2$ each independently indicate a hydrogen atom, lower alkyl group having 1 to 3 carbon atoms.

The compounds in the general formula (II), which are intermediates of this preparation method, are also novel and can be prepared from the compounds represented by the general formula (III) according to the known method (Japan Kokai No. 60-243088).

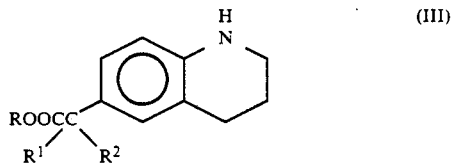

wherein R, $R^1$ and $R^2$ have the same meanings described above.

Moreover, the compounds represented by the general formula (I) can be converted to the corresponding salts by the treatment with acid or alkali. The acid may be an inorganic acid such as, for example hydrochloric acid, sulfuric acid or phosphoric acid, or an organic acid such as, for example methanesulfonic acid, lactic acid, acetic acid, citric acid or tartaric acid. The alkali may be an alkali metal such as, for example, sodium or potassium.

The invention will be illustrated based on concrete examples, but the invention is not confined to following examples.

EXAMPLE 1

Ethyl 5,6-dihydro-1,2-dioxo-4H-pyrrolo[3,2,1-ij]quinolin-8-ylacetate

To the refluxing mixture of oxalyl chloride (0.3 ml) in dry tetrahydrofuran (THF; 15 ml) was added ethyl 1,2,3,4-tetrahydroquinolin-6-ylacetate (500 mg) in dry THF (5 ml) dropwise. The mixture was refluxed for 4 hours after addition was completed, then cooled to room temperature and concentrated under reduced pressure. The residue was dissolved in carbon disulfide (20 ml) and added aluminum chloride (610 mg) portionwise. The mixture was refluxed for 4 hours and allowed to stand for overnight at room temperature. After decantation of the solvent, ice water (20 ml) was added to the residue. The mixture was extracted with chloroform and dried over anhydrous sodium sulfate. Evaporation of chloroform afforded the title compound. The compound was recrystallized from acetonitrile to give 490 mg (75%) of dark red needles, mp 124°-125° C.

Analysis (%) for $C_{15}H_{15}NO_4$, Calcd. (Found): C, 65.92 (65.83); H, 5.53 (5.52); N, 5.13 (5.12).

EXAMPLE 2

8-Carboxy-1,2,3,4-tetrahydroquinolin-6-ylacetic acid

To a solution of ethyl 5,6-dihydro-1,2-dioxo-4H-pyrrolo[3,2,1-ij]quinolin-8-ylacetate (21.5 g) and sodium hydroxide (18.5 g) in water (1 liter) was added 35% hydrogen peroxide solution (10 ml) and stirred for 3 hours at room temperature. The mixture was acidified at pH 2 with concentrated hydrochloric acid, resulting precipitate was collected by filtration, washed with water and dried to yield 17.6 g (95.1%) of the title compound. The compound was recrystallized from ethanol to give pale yellow needles, mp 210°-211° C.

Analysis (%) for $C_{12}H_{13}NO_4$, Calcd. (Found): C, 61.27 (61.21); H, 5.57 (5.62); N, 5.95 (5.90).

Further, the following experiments will illustrate the effectiveness of the compound of the present invention.

EXPERIMENT 1

Therapeutic Effect on Adjuvant Arthritis in Sprague Dowley Rats

Adjuvant arthritis was induced by intradermal injection of heat-killed *Mycobacterium butyricum* (0.6 mg/rat) suspended in liquid paraffin into the right hind foot pad of female rats (8 week of age). The compound of this invention suspended in 0.3% carboxymethylcellulose solution was orally administered once a day for 7 days during days 14 to 20 after adjuvant injection. Left hind paw volume was measured by the water immersion method.

As shown in Table 1, administration of the Example 2 compound reduced the swelling of left (uninjected) hind paw.

TABLE 1

| Compound | Dose (mg/kg) | N | Increase in left hind paw[1] Day 17 | Day 21 |
| --- | --- | --- | --- | --- |
| control (adjuvant) | — | 8 | 1.54 ± 0.21 | 1.35 ± 0.16 |
| Example 2 | 10 | 8 | 0.96 ± 0.29 | 1.03 ± 0.31 |
| Example 2 | 50 | 8 | 1.22 ± 0.25 | 1.15 ± 0.32 |

[1])volume (ml), Mean ± S.E.

EXPERIMENT 2

Inhibition of Bone Damage in Adjuvant Arthritis

Adjuvant arthritis was induced by the same manner as Experiment 1. The schedule of administration was also same in Experiment 1. On day 27, all rats was killed and radiographs of hind paws were taken using a soft X-ray apparatus. The degree of bone damage was assessed blindly on a scale (grades 1 through 4) based on the "cotton wool appearance" surrounding the distal limb joints.

As shown in Table 2, the Example 2 compound significantly inhibited the progression of bone damage induced in the adjuvant arthritis.

TABLE 2

| Compound | Dose (mg/kg) | N | Bone damage score on Day 27 (Mean ± S.E.) | |
| --- | --- | --- | --- | --- |
| | | | Non-injected paw | Injected paw |
| control (adjuvant) | — | 8 | 1.63 ± 0.38 | 3.38 ± 0.26 |
| Example 2 | 5 | 6 | 1.33 ± 0.49 | 3.33 ± 0.33 |
| Example 2 | 10 | 8 | 1.00 ± 0.33 | 2.25 ± 0.37* |

*Significantly different from adjuvant control, P <0.05.

What is claimed is:

1. Cyclic anthranilic acid acetic acid derivative of the following formula (I),

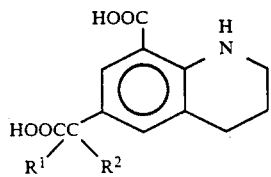

wherein $R^1$ and $R^2$ each independently indicate a hydrogen atom or lower alkyl group having 1 to 3 carbon atoms; or the acid or alkali salt thereof.

2. A process for preparation of the compound of the following formula (I),

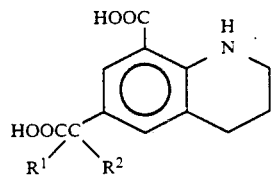

wherein $R^1$ and $R^2$ each independently indicate a hydrogen atom or lower alkyl group having 1 to 3 carbon atoms; or the acid or alkali salt thereof; which comprises hydrolysing the compound of the following formula (II),

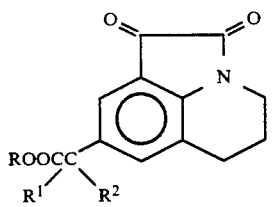

wherein R indicates a hydrogen atom or lower alkyl group having 1 to 3 carbon atoms, $R^1$ and $R^2$ have the same meanings described above; followed by decarbonylation in the presence an oxidizing agent.

3. A pharmaceutical composition to treat autoimmune deseases containing a compound of the following formula (I),

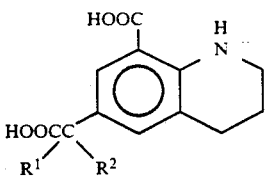

wherein $R^1$ and $R^2$ each independently indicate a hydrogen atom or lower alkyl group having 1 to 3 carbon atoms; or the acid or alkali salt thereof; and an inert pharmaceutically acceptable carrier.

4. An antirheumatic pharmaceutical composition containing a compound of the following formula (I),

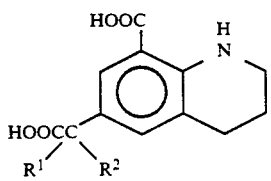

wherein $R^1$ and $R^2$ each independently indicate a hydrogen atom or lower alkyl group having 1 to 3 carbon atoms; or the acid or alkali salt thereof; and an inert pharmaceutically acceptable carrier.

5. A therapeutic or prophylactic pharmaceutical composition to treat metabolic bone diseases containing a compound of the following formula (I),

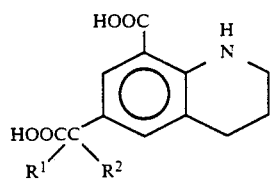

wherein $R^1$ and $R^2$ each independently indicate a hydrogen atom or lower alkyl group having 1 to 3 carbon atoms; or the acid or alkali salt thereof; and an inert pharmaceutically acceptable carrier.

6. A method of treating autoimmune diseases in a patient in need thereof which comprises administering an effective amount of the compound of claim 1 to said patient.

7. A method of treating rheumatoid arthritis in a patient in need thereof which comprises administering an effective amount of the compound of claim 1 to said patient.

8. A method of treating metabolic bone diseases in a patient in need thereof which comprises administering an effective amount of the compound of claim 1 to said patient.

* * * * *